(12) United States Patent
Gysler et al.

(10) Patent No.: US 6,905,869 B2
(45) Date of Patent: Jun. 14, 2005

(54) METHOD FOR INTRODUCING RECESSIVE PROPERTIES INTO THE GENETIC BACKGROUND OF INDUSTRIAL BAKER'S YEAST

(75) Inventors: Christof Gysler, Blonay (CH); Peter Niederberger, Epalinges (CH)

(73) Assignee: Nestec S.A., Vevey (CH)

( * ) Notice: Subject to any disclaimer, the term of this patent is extended or adjusted under 35 U.S.C. 154(b) by 512 days.

(21) Appl. No.: 09/837,239

(22) Filed: Apr. 18, 2001

(65) Prior Publication Data
US 2002/0004243 A1 Jan. 10, 2002

(30) Foreign Application Priority Data
Apr. 20, 2000 (EP) ............................................ 00108636

(51) Int. Cl.[7] .................................................. C12N 1/18
(52) U.S. Cl. .................... 435/255.1; 435/440; 435/471; 435/243; 435/252.3; 435/254.1; 435/255.2
(58) Field of Search .................................. 435/440, 471, 435/243, 252.3, 254.1, 255.1, 255.2

(56) References Cited

U.S. PATENT DOCUMENTS

| 5,399,492 A | 3/1995 | Gysler et al. |
| 5,480,798 A | 1/1996 | Gysler et al. |
| 5,776,526 A | 7/1998 | Baensch et al. |
| 5,827,724 A | 10/1998 | Gysler et al. |
| 6,410,303 B1 * | 6/2002 | Takano et al. .......... 435/254.21 |

FOREIGN PATENT DOCUMENTS

| EP | 0 442 575 A1 | 8/1991 |
| EP | 0 556 905 A1 | 8/1993 |

OTHER PUBLICATIONS

Yoshinobu Tani et al., A Novel Method for Breeding Polyploid Cells by Heat-induced Endomitotic Diploidization in *Saccharomyces cerevisiae*, Bioscience (XP -002149562, Biotechnology and Biochemistry, vol. 57, No. 12, 1993, pp. 2063–2066.

* cited by examiner

*Primary Examiner*—James Ketter
*Assistant Examiner*—David A. Lambertson
(74) *Attorney, Agent, or Firm*—Winston & Strawn LLP (57) ABSTRACT

A method of introducing a property of a particular yeast strain, based on a recessive allele, into the genetic background of an industrial baker's yeast; as well as yeast strains obtainable according to the method. In particular, a method is disclosed to introduce an lti-property into the genetic background of industrial baker's yeast. The novel strains obtained according to the method may be used for the preparation of a dough and for the manufacture of baked products therefrom, such as on an industrial scale.

8 Claims, 3 Drawing Sheets

Figure 1: Initial $CO_2$ formation rates of LTI strains grown with the dough screening procedure Figure 2: Initial $CO_2$ formation rates of LTI strains grown with the fed-batch procedure Figure 3: Gas development in dough by LCG2 in the "active" approach

METHOD FOR INTRODUCING RECESSIVE PROPERTIES INTO THE GENETIC BACKGROUND OF INDUSTRIAL BAKER'S YEAST

FIELD OF THE INVENTION

This invention relates to a novel method of introducing a property of a particular yeast strain, which property is based on a recessive allele, such as an lti-property, into the genetic background of an industrial baker's yeast. The invention further relates to yeast strains obtainable according to the method described, which may be used for the preparation of a dough and for the manufacture of baked products therefrom on an industrial scale.

BACKGROUND OF THE INVENTION

A variety of different dough products are presently available to consumers for production of different sorts of baked stuffs, such as pizza-crusts, buns, croissants, etc. These products may generically be divided into two major groups: 1) those goods based on the process of leavening the dough, namely those goods wherein the dough is leavened by means of chemical agents, and 2) those goods wherein the dough is leavened by the fermentative activity of baker's yeast contained in the dough.

The use of chemicals as the leavening agent for a dough has been commonly used and has the advantage that the chemicals' behavior is based on a predictable chemical reaction, allowing for a specific control of the volume of carbon dioxide produced to leaven the dough. Since the amount of carbon dioxide production and also the moment at which said production is to take place may be controlled, the manufacture of the baked products from the dough can be carried out even after a long shelf life thereof.

The final baked good products obtained therewith are inferior in overall quality as compared to dough products leavened by means of baker's yeast. In particular, the texture of such products is often not acceptable to customers and in addition, the products lack flavor compounds produced by the yeast during its leavening action.

For this reason, producers of edible baked goods try to avoid the use of such chemicals in their products and rely instead on the use of baker's yeast. Unfortunately, products containing ordinary baker's yeast suffer from a variety of different problems inherent to the utilization of "live microorganisms."

One of these problems is that the activity of yeast in a dough cannot be controlled straightforwardly. For this reason, yeast containing dough compositions may be stored only for a limited period of time because under common conditions of storage, such as room temperature or even lower temperatures (e.g., storage in a refrigerator), and ordinary baker's yeast shows substantial activity resulting in a consistent production of carbon dioxide. This continuous activity of the ordinary baker's yeast beyond the desired degree of proofing negatively affects the organoleptic and Theological properties of the dough, which results in unacceptable final products from the point of view of taste and texture.

One approach taken to avoid this particular setback was to store a yeast containing dough, optionally in pre-baked form, at freezing temperatures of about −20° C., so as to reduce the activity of the yeast to a minimum.

To this end, European Patent No. 0 442 575 instructs dough composition use with the substrate limiting concept. Accordingly, a dough is leavened with a maltase negative yeast until all of the directly fermentable components thereof are consumed, the dough is then frozen for long term storage. Before consumption, the frozen dough is thawed and further leavened by means of chemical agents. This approach also proved to be unsatisfactory as products that are prepared from frozen dough compositions are not as convenient for the consumer as fresh (e.g., refrigerated) dough products. The frozen dough must be thawed and, in most instances, pre-proofed prior to baking. Pre-proofing requires consumer monitoring so as to avoid excessive proofing of the dough.

Moreover, the texture of the final baked products derived from frozen doughs has been shown to be inferior as compared to products produced from non-frozen doughs. In addition, the characteristic flavor associated with yeast leavening is also inferior or often not present at all in final baked products derived from frozen doughs.

Another approach taken to overcome the storage problem of fresh, yeast containing dough compositions was the development and utilization of low temperature inactive (lti) yeast strains in dough. Lti-yeast strains are yeast strains that are essentially inactive at low temperatures, but retain their activity when brought to higher, or proofing, temperatures.

European Patent No. 0 487 878 describes a process for constructing yeast strains with lti-properties, wherein a strain of *Saccharomyces cerevisiae* is subjected to a mutagenic treatment. The treatment dictates that at least one mutant with an lti-property is selected and backcrossed at least once with a wild type haploid strain of *Saccharomyces cerevisiae* having an opposite mating type. At least two of the backcross segregants having lti-properties and opposite mating types are then selected and are crossed at least once. This mutagenic treatment results in the selection of a diploid strain having growth potential, an lti-property, and the ability to raise a dough.

Further, the construction of different lti-derivatives have been described. European Patent No. 0 663 441 describes a process for constructing lti-strains that react more sluggishly with the maltose contained in the dough. These sluggish lti-strains may be obtained by first crossing a haploid *Saccharomyces cerevisiae* that possesses an lti-property with a haploid *Saccharomyces cerevisiae* strain that has an active maltase gene under catabolic repression, then crossing the segregants, and finally selecting a diploid strain with an lti-property, an active Mal-phenotype (Mal$^+$) expressing the gene coding for maltase either inducibly (wild-type) or constitutively, and growth potential.

From the industrial manufacturer's point of view, one of the major problems encountered in preparing dough compositions or edible baked products therefrom resides in that yeast strains allowing for large scale production at reasonable expenses have to be utilized. The yeast strains needed for industrial scale production comprise of a high yield, a high biomass production, or a good dryability. Presently, there are only a limited number of strains commercially available with such characteristics that enable said dough composition production on an industrial scale. Examples of such strains are Levure Boulangeère Bleue (available from Lesaffre et Cie, Paris, France), Fermipan (Fermipan Red, available from Gist-Brocades, Delft, The Netherlands), or HS (available from Hefe Schweiz, Stettfurt, Switzerland). The genetic reason for this lack of acceptable yeast strains is that the genes which cause these properties are not yet elucidated. The available industrial yeast strains are difficult to modify for new particular properties, such as low temperature inactivity, glucose-de-repression, trehalase deficiency, or one or several auxotrophies.

Therefore, there is a need in the art to enable a skilled person to introduce such properties into the genetic background of industrial bakers' yeast. Since these properties of yeast strains are most often based on a recessive allele, a combination of such a property with the properties of an industrial strain is not an easy task to achieve. The difficulty of the task resides in providing a method to introduce properties of known strains into the genetic background of industrial's baker's yeast, which results in novel yeast strains having both the property afforded by the recessive allele and the properties provided by industrial baker's yeast. Thus, it would be desirable to determine a process by which properties of known yeast strains can be introduced in the genetic background of baker's yeast.

SUMMARY OF THE INVENTION

The invention relates to a method for modifying stable industrial baker's yeast including selecting a yeast having a desired property based on a recessive allele, diploidizing the selected yeast and selecting for a homozygote mating type from the diploidized yeast, diploidizing an industrial baker's yeast and selecting for a homozygous mating type from the diploidized industrial baker's yeast, mating the diploidized yeast and diploidized industrial baker's yeast having an opposite mating type to obtain a tetraploid zygote, sporulating the tetraploid zygote, and selecting the sporulated tetraploid zygote strains exhibiting the desired property to provide the modified stable industrial baker's yeast having the desired property.

Generally, the desired property is based on a recessive allele of a gene which leads to at least one of increased biomass production, cell separation, or drying during at least one of yeast dough production, storage, or baking so as to improve the performance of the industrial baker's yeast. The gene is preferably a catabolite repressor gene, a gene coding for neutral or acid trehalase, a gene coding for a biosynthetic enzyme, or a gene that in allelic form leads to a lti-property.

To achieve the desired property, the sporulated zygote strains exhibiting the desired property are mated with an opposite mating type. A further polyploidizing step can provide industrial advantages including facilitated filtering due to the enlarged yeast size.

In another embodiment of the invention, a stable baker's yeast is obtained through the above-noted method. In a preferred embodiment, the stable baker's yeast is diploid or tetraploid.

In another embodiment of the invention, the desired property of the yeast strain is advantageously an lti-property, so that the stable baker's yeast has an lti-property. The $CO_2$ production profile of the stable baker's yeast is advantageously less than 3 ml/g dough per hour at refrigeration temperatures of about 3° C. and 12° C. The $CO_2$ production profile is preferably higher than the activity of either parent yeast strain and preferably less than 1 ml/g dough per hour. Advantageously, the stable baker's yeast constitutively or inducibly expresses maltase. Preferably, the stable baker's yeast obtained is one of accession number FCL 313 (NCIMB 41002), CL14 (NCIMB 41032), or CL18 (NCIMB 41033).

The invention also relates to dough compositions including the stable baker's yeast obtained through the method described herein.

The invention further relates to a method for obtaining baked dough products by providing the dough composition including the stable baker's yeast and baking the dough composition to provide the one or more baked dough products. Still another aspect of the invention concerns the baked dough products obtained through such a method.

BRIEF DESCRIPTION OF THE DRAWINGS

Further features and advantages of the invention can be ascertained from the following detailed description that is provided in connection with the drawings described below.

DETAILED DESCRIPTION OF THE INVENTION

The present invention advantageously solves this problem in the art, by providing a novel method for modifying industrial baker's yeast comprising of selecting a yeast having a desired property based on a recessive allele, diploidizing the selected yeast and selecting the diploidized yeast for a homozygote mating type, diploidizing an industrial baker's yeast and selecting the diploidized industrial baker's yeast for a homozygote mating type, mating strains obtained with an opposite mating type to obtain a tetraploid zygote, sporulating the zygote obtained, and finally selecting for strains exhibiting the recessive property. Optionally, the finally selected strains having an opposite mating type can mated to achieve certain preferred properties.

The method of the invention offers significant advantages over the prior art. For example, the invention provides a method to modify an industrial baker's yeast whereby less yeast is needed to leaven a dough due to increased activity of the yeast as compared to parent strains. The invention also permits increased storage durations, which, in turn, reduces the risk of overproofing the dough while in storage.

The desired properties, known to be based on recessive alleles and to be combined with the properties of industrial baker's yeast are properties arising from inactive glucose repressors or from inactive trehalase(s), auxotrophies, and lti-properties. According to a preferred embodiment the allele to be introduced is an lti-allele. One example of an lti-allele is a catabolite repressor gene (e.g., MIG1 or HXK2) which de-represses the maltose utilization genes and allows for a quicker adaptation of the sucrose-grown yeast to the main carbon source in the flour. Another example of an lti-allele is a non-functional allele of a gene involved in trehalose degradation (e.g., neutral trehalase (NTH1) or acid trehalase (ATH1)), which avoids rapid trehalose degradation and so indirectly increases the trehalose content of the yeast rendering it more resistant to stress conditions (i.e., drying, freezing, resistance to toxic levels of ethanol). Yet another example of an lti-allele is an auxotrophic allele (e.g., ura3 or leu2), which allows for a selection of plasmids.

The present invention also provides for novel yeast strains, which are obtainable according to the present method. These strains in particular retain the "industrial capability" exhibited by the parent "industrial strain" comprising a biomass production of about 0.1 g to 0.5 g derived from 1 g sugar in a fed batch process, no substantial production of ethanol, during fed batch yeast biomass production, an activity in a dough consisting of 56.4% $_{w/w}$ flour, 42.3% $_{w/w}$ water, 1.15% $_{w/w}$ NaCl 0.15% $_{w/w}$ $(NH_4)_2SO_4$ leading to a carbon dioxide production when using 160 mg dry yeast in 35 g of the model dough of at least 30 ml at 30° C. during an incubation period of 2 hours.

The yeast strains thus obtained exhibit both the properties of the parent industrial strain and the property derived from the recessive allele of the strain exhibiting the property to be introduced into the genetic background of industrial baker's yeast, such as auxotrophy, glucose de-repression, trehalase inactivity. The property introduced is preferably an lti-mutation. According to a preferred embodiment of the invention, the yeast strain is a tetraploid, which is larger in size and easier to filter during production.

The yeast strains thus obtained preferably have the capability to produce carbon dioxide at refrigerator temperatures ranging from about from about 3° C. to 12° C. of less than 3 ml, preferably less than 1 ml $CO_2$/per hour/per g dough (160 mg dry yeast in 35 g of a dough containing (w/w) 56.4% flour, 42.3% water, 1.15% NaCl and 0.15% $(NH_2)_2SO_4$. Preferably, the $CO_2$-production profile comprising an activity at leavening temperatures, which is higher than the activity of the strains they are derived from (i.e., the parent industrial strains and/or the parent lti-strain), further an activity at refrigerator temperature (about 3° C. to 12° C.), which is higher than compared to the activity of the parent lti-strain. Yeast strains exhibiting such a $CO_2$-production profile have proven to provide an additional advantage in the composition of dough. With these strains, it is possible to include a minor amount of yeast in the dough composition while, due to the increased activity of the yeast at temperatures of about 30° C. (leavening temperatures) still achieving the same results when leavening the dough. Alternatively, the storage lifetime of the dough composition may be prolonged, since less material of yeast is present in the dough, which will also reduce the risk of overproofing the dough during storage.

Preferably, the baker's yeast obtained by the method of the invention is FCL 313 (NCIMB 41002), CL14 (NCIMB 41032) or CL18 (NCIMB 41033), each of which has been deposited with the National Collection of Industrial and Marine Bacteria Ltd.(Aberdeen, Scotland, UK) according to the Budapest Treaty.

The novel yeast strains obtained by the method of the invention may be used for the preparation of dough compositions and eventually for the manufacture of baked products. Thus the present invention shall also encompass the products that have been prepared with the yeast strains according to the present invention.

Although not required, the yeast strains obtained by the method of the invention express the maltase gene constitutively or non-constitutively. On the other hand, in order to avoid an excessive activity of the yeast deriving from, for example, the consumption of maltose present in the dough, the parent lti-yeast may be selected to be repressed by other components present. In the dough compositions containing the lti-yeast strains according to the present invention other lti-yeast strains having distinct phenotypes/genotypes may additionally be employed. Consequently, for example, a mixture of the novel lti-strains together with common lti-strains, such as Mal$^-$ lti-strains (yeast strains that are not capable of metabolizing maltose) or Mal$^+$ lti-strains, may be utilized. The skilled person may select an appropriate mixture from the lti-strains available, in agreement with the factors influencing the yeast activity, such as the presence of maltose, the temperature, optional other sugars present, etc., to adapt the dough composition to the $CO_2$-profile desired.

The method of preparing dough compositions includes mixing water, flour and at least one of the novel yeast strains. The flour utilized may be any flour commercially available, though it might in case be advantageous to use flour, which contains a certain amount of damaged starch, which may serve as a sugar source for yeast strains present. Water is generally added according to the hydration capacity of the flour and the potential influence of other components contained in the dough, which may increase or decrease this capacity, until a workable dough is formed. The dough may optionally contain salts, preferably sodium chloride, in an amount of up to about 8 parts by weight, based on the amount of flour being 100 parts by weight. Further, ethanol may be included in an amount of up to about 8 parts by weight, again based on the amount of flour being 100 parts by weight.

The yeast may be added as dry yeast, rehydrated in all or in a part of the water used for preparing the dough. The use of a press cake, having a dry matter content of about 20% to 40% or the use of yeast-cream having a dry matter content of about 10% to 20% may likewise be used, with the water to be added to the flour being adjusted correspondingly.

In the first step of the method, the yeast strain exhibiting the desired property, based on a recessive allele, is selected. This strain must be present in a diploid form being homozygous for its mating type. Thus, the following theoretical options can occur:

1. The strain is already diploid and also shows a homozygous mating type, i.e. either a/a or α/α; or
2. The strain is diploid or tetraploid, but not homozygous for its mating type and must be made to order accordingly.

When starting from a diploid yeast strain, which is not homozygous for its mating type or when even starting from a tetraploid strain, these strains have to be brought first to a haploid form. This may be achieved by effecting sporulation of the strains according to methods well known in the art, such as described in Sherman, F. G. R. et al., A Laboratory Course Manual in Yeast Genetics (1986), Cold Spring Harbor Laboratory Press, Cold Spring Harbor, N.Y. This method includes ascus dissection with a micromanipulator. To accomplish this, a loop of a sporulated culture is transferred into sterile water and snail juice (Suc d'Hélix pomatia, Biosepra, France) is added thereto. Digestion is effected for several minutes until spores start getting released from the asci, which are then separated and streaked out on agar plates. Upon incubation the spores will yield colonies, which consist of haploid yeast cells.

These haploid segregates, exhibiting either an a or an α mating type, which may be checked in crosses with standard strains, such as X2180-1A (a) or X2180-1B (α) (obtained from Yeast Genetic Stock Center, Department of Molecular and Cellular Biology, Division of Genetics, University of California, Berkeley, Calif. 94720, USA). The mating type of a segregant is defined by its ability to form zygotes with a tester strain of the opposite mating type and its inability to form zygotes with a tester strain of the same mating type. Strains exhibiting the desired property may then be selected.

The corresponding haploid strains are again diploidized, which may be effected by utilizing the phenomenon of spontaneous diploidization (cf. Sherman, supra). To this end, the respective haploid strains may be grown in a suitable liquid medium for several weeks at ambient or slightly raised temperatures under agitation and subculturing regularly at intervals. Every now and then the cells may be plated on YPD plates (below) and growing colonies can be screened for especially large varieties. When large colonies are found, their ploidy may be tested by back-crossing with tester strains of known ploidy. A strain of unknown ploidy (haploid or diploid) still exhibiting a mating type (a or a/a; α or α/α) is crossed to tester strains of known ploidies (haploid or diploid). The resulting zygotes will be either diploid (haploid×haploid), triploid (haploid×diploid) or tetraploid (diploid×diploid). These zygotes are sporulated and a representative number of spores isolated by ascus dissection as described above. Triploid zygotes are easily identified by their drastically reduced spore viability (normally up to about 10%) while zygotes of even numbered ploidies (diploid or tetraploid) usually give spore viabilities above 50%. Therefore, a haploid segregant will yield high spore viabilities in crosses with a haploid tester strain but low spore viabilities with a diploid tester. In contrast, a diploid segregant yields low spore viability with a haploid tester but high spore viability with a diploid tester.

On the other hand, when starting with a haploid strain only the diploidization as detailed above has to be effected.

The diploid strains thus obtained having either an a/a or an α/α mating type and being homozygous for the desired trait to be introduced into the genetic background of baker's yeast may then be used for the further process steps.

The industrial baker's yeast step includes sporulating a tetraploid industrial baker's yeast (e.g., LBB, H S, Fermipan). Diploid segregants exhibiting a mating type, thus being homozygous for either a/a or α/α, are selected.

The diploidized yeast strains having the specific trait and the diploidized industrial baker's yeast, each of which having a particular homozygous mating type, are combined such that strains with an opposite mating type, (i.e., a/a with α/α) are combined in a manner known (Sherman, supra) to yield a tetraploid zygote aa/αα.

The tetraploid zygotes, resulting from such a crossing of the diploid parent strains are again sporulated and the meiotic spores are isolated.

The spores obtained by the sporulation are then selected for the specific trait to be conferred to the industrial background of baker's yeast.

Although not required, the diploid strains obtained by following the method of the invention may be further polyploidized. To further polyploidize, the selected yeast strains exhibiting the recessive property are tested to be homozygous for their mating type, and strains having an opposite mating type are crossed. Polyploidized strains have an additional industrial advantage of easier filtering because of their enlarged size.

Any suitable industrial strain may be utilized, such as the commercially available strains Fermipan Standard ("Fermipan Red", an instant active dry yeast, available from GistBrocades, Netherlands) or LBB (Levure Boulangeère Bleue, available from Lesaffre, France) or HS (obtainable from Hefe Schweiz, CH). Based on his/her own technical skill and experience and depending on the respective genetic background into which the lti property is to be introduced, the skilled person will select the appropriate strain. Since a number of the known industrial strains are of tetraploid nature, they must be diploidized before combining them with the diploid strains having the desired trait.

In a preferred embodiment of the invention, the yeast strain exhibiting the desired trait is an lti-strain, such as the strain L500 (NCIMB 40329) or LCG22 (NCIMB 40612). The processes of production are described in detail in EP-0 487 878 and EP 0 663 441, respectively. The documents are included herein by way of reference.

The word "about", as used herein, refers to both numbers in a range of numbers.

EXAMPLES

These and other aspects of the present invention may be more fully understood with reference to the following examples, which are merely illustrative of preferred embodiments of the present invention and are not to be construed as limiting the invention.

Example 1
Construction of Novel Strains

In order to introduce industrial characteristics in a lti-yeast a lts500-lti-mutant (NCIMB 40613) has been utilized having the following genotype:

α lts500

This strain was crossed to the maltose fermenting strain 1403-7A a MAL4c ura3

(obtained from Yeast Genetic Stock Center, Department of Molecular and Cellular Biology, Division of Genetics, University of California, Berkeley, Calif. 94720, USA) (capital letters indicate dominant alleles, lowercase letters indicate recessive alleles).

The zygote was sporulated (Sherman, supra) and meiotic spores were isolated as follows. A loop of the sporulated culture was suspended in 0.2 ml of sterile water contained in an Eppendorf tube and about 0.02 ml to 0.04 ml snail juice (Suc d'Hélix pomatia, Biosepra, France) were added. The suspension was incubated at room temperature for about 4 min to 15 min. The time varied from strain to strain, while the appropriate time was observed by means of a microscope and was considered to be about fitting when spores started to get released from asci. This was manifested by "explosion waves" in the liquid and the spores packages getting more loosely arranged. After the incubation, 1 ml of sterile water was added and the suspension was centrifuged for about 5 min. The supernatant was sucked off and the pellet was suspended in about 0.5 ml sterile water, centrifuged and the supernatant was discarded. After suspending the spores in about 0.5 ml of sterile water the suspension was streaked with a fine platinum loop at the edge of a dissection agar patch (2% glucose, 1% yeast extract, 0.5% peptone, 2% agar) that has been cut to the appropriate size. The tetrads were dissected with spacings of 2.5 mm between the spores and 3 mm between each tetrad using a Leitz Micromanipulator (Leitz, Germany). The agar patches were transferred on YPD (YPD-full medium (solidifed with 2% Bacto agar (Difco); 1% Bacto yeast extract (Difco), 2% Bacto peptone (Difco), 2% glucose) agar plates and incubated at 30° C. until the spores formed colonies, that were subsequently transferred with tooth picks to new YPD agar plates (supra) for further analysis.

The haploid segregants thus obtained were tested for their mating type, a or α, respectively, by crossing them with standard strains, such as X2180-1A (a) or X2180-1B (α) available from Yeast Genetic Stock Center, Department of Molecular and Cellular Biology, Division of Genetics, University of California, Berkeley, Calif. 94720, USA).

The testing was carried out as follows. The strains were grown overnight on YPD agar plates (1% Difco Bacto Yeast Extract, 2% Difco Bacto Peptone, 2% glucose, 2% agar). Small aliquots of the segregant were mixed with a small aliquot of the a-tester and with a small aliquot of the α-tester on a YPD plate with the help of a sterile wooden toothpick.

After 5 to 6 hours of incubation at 30° C., both mixes were analyzed microscopically upon the formation of zygotes.

Since the parent strain was homozygous for the lti-mutation, all segregants showed a clear lti-phenotype and were either maltose fermenting (Mal⁺) or maltose non-fermenting (Mal⁻) and either Uracil prototrophic (URA3) or auxotrophic (ura3), as determined by standard procedures (Sherman, F. G. R. et al., A Laboratory course manual in yeast genetics (1986), Cold Spring Harbor Laboratory Press, Cold Spring Harbor, N.Y.).

For obtaining diploid isolates from the various haploid strains obtained the phenomenon of spontaneous diploidization was utilized. To this end, the given haploid strain was grown in a liquid YPD medium (supra) for 12 weeks at about 30° C. under agitation while subculturing regularly at intervals of about 3 to 4 days. Every now and then cells were plated on YPD plates and growing colonies were screened for especially large varieties. When large colonies are found, their ploidy was tested by back-crossing with haploid (X2180-1A (a), X2180-1B ($\alpha$), supra) or diploid (X2180-1A/1A (a/a), X2180-1B/1B ($\alpha/\alpha$), ETHZ strain collection, Eidgenossisch Technische Hochschule, Zurich, Switzerland) tester strains.

In consequence, strains were selected that showed the following properties:
a) the diploids were homozygous for the lts500 mutation and exhibited a clear lti-phenotype;
b) the diploids were homozygous for the URA3 wild type allele and had a prototrophic phenotype;
c) the diploids carried at least one Mal4c allele to give a maltose fermenting (Mal⁺) phenotype;

The selection of strains showing the above properties has been carried out as follows: Mal and Ura phenotypes were determined by standard procedures (Sherman, F. G. R. et al., A Laboratory course manual in yeast genetics (1986), Cold Spring Harbor Laboratory Press, Cold Spring Harbor, N.Y.).

The lti-phenotype is analyzed by streaking a small layer of yeast cells grown overnight on a YPD agar plate (1% Difco Bacto Yeast Extract, 2% Difco Bacto Peptone, 2% glucose, 2% agar) on a fresh YPD agar plate. The growth response is checked after 2 to 3 weeks incubation at 8° C.

In order to combine the lti-phenotype with a globally industrial genetic background a strain having the following lti-genotype has been selected and has been used for the further experiments:
RD1483-2C-2: $\alpha/\alpha$ lts500/lts500 MAL4c MAL4c URA3/URA3

This strain has been combined with diploid segregates of the following commercial baker's yeast strains:
(1) LBB (Levure Boulangeère Bleue, Lesaffre)
(2) Fermipan Standard (Gist Brocades),
which diploid segregants have been obtained by sporulation and subsequent isolation of diploid ascospores. Diploid segregants exhibiting an a mating type (thus being homozygous a/a) were chosen for crossing to the diploid lti-strain RD1483-2C-2.

The mating of the above lti-strain with various strains of the above generic industrial strains has been carried out as follows. Strains of opposite mating type were streaked out on YPD agar plates and the plates were incubated at 30° C. over night. A small, but equal amount of each strain to be mated was mixed on a YPD agar plate and incubated at 30° C. for 5 to 6 hrs. The formation of zygotes was checked under the microscope. The zygotes visualized were subsequently pulled out by means of a Leitz micromanipulator (Leitz, Germany).

The following tetraploid segregates could by isolated thereby:

| 1) Segregates from LBB (Levure Boulangeère Bleue, Lesaffre) | | |
|---|---|---|
| F-7 | to give zygote | RD83-7 |
| F-24 | | RD83-24 |
| F-28 | | RD83-28 |
| FZ 15 | | FD 1583 |
| FZ 24 | | FD2483 |
| 2) Segregates from Fermipan Standard (Gist Brocades) | | |
| FP5 | to give zygote | PD583 |
| FP6 | | PD683 |
| FP 10 | | PD1083 |
| FP2O | | PD2083 |

The tetraploid zygotes were sporulated and meiotic spores were isolated as described above with reference to the sporulation of diploid lti-yeast strain L 500. The spores displaying a lti-phenotype in a first assay were analyzed further for their mating and sporulation behavior, respectively.

Example 2

Selection of the Strains For Industrial Properties

To determine the performance of a strain in an industrial fed-batch process, a test was applied wherein the growth rate in aerobic shake-flask cultures with ethanol as carbon source and acetate as inhibitory substance was measured. The concentration of ethanol was chosen at a sub-toxic level of 0.7%, while acetate concentration (present as free acid by buffering the pH of the medium to 4.0) was optimized in a way that the growth rate difference between a well-performing reference strain (Levure Boulangeère Bleue (LBB), Lesaffre) and a poorly-performing reference strain (X2 180, Yeast Genetic Stock Center, UC Berkeley) was maximal. In each test series, both reference strains were included and the performance of the tested strains was expressed in percent of the growth rate of the well-performing, industrial strain LBB.

The cells of the strain to be tested were pre-cultivated in a test tube in 5 ml YPD (1% $_{w/v}$ Difco Bacto Yeast Extract, 2% $_{w/v}$ Difco Bacto Peptone, 2% $_{w/v}$ glucose) overnight at 30° C. on a rotary shaker at 190 rpm. Of this culture, 1 ml was used to inoculate a shake-flask preculture (500 ml Erlenmeyer flasks with 4 baffles at the bottom) with 100 ml volume of NEA-medium (0.67% $_{w/v}$ Difco Yeast Nitrogen Base w/o amino acids, 1% $_{w/v}$ Na₂-succinate, 1.12% $_{w/v}$ HCl 5M, 0.7% $_{w/v}$ ethanol (added after autoclaving)) and incubation was continued for 24 hrs at 30° C. on a rotary shaker at 190 rpm. The final test cultures (500 ml Erlenmeyer flasks with 4 baffles at the bottom) were started by inoculation of 100 ml NEA-medium (0.67% $_{w/v}$ Difco Yeast Nitrogen Base w/o amino acids, 1% $_{w/v}$ Na₂-succinate, 1.12% $_{w/v}$ HCl 5M, 0.7% $_{w/v}$ ethanol, 0.3% $_{w/v}$ Glacial acetic acid (ethanol and acetic acid added after autoclaving)) in a way that OD$_{600}$ was about 0.1. Incubation at 30° C. and 190 rpm on a rotary shaker was continued over 10 hrs and the OD$_{600}$ was measured at intervals of 2 hrs. The growth rate was established during the exponential growth phase of the cultures. In comparison to LBB (100%), the growth rate of the deposited strains amounted to:

| (LBB    | 100%)             |
|---------|-------------------|
| FCL313  | 137%              |
| CL14    | 165%              |
| CL18    | 85%               |
| (X2 180 | approx. 30% to 40%) |

Example 3
Selection of Strains For lti-properties

Cells were grown in two stages of shake flask culture. One step comprised a pre-culture, wherein 0.1 ml of a negative 80° C. glycerol-freeze cell suspension of each strain was inoculated in 200 ml YD medium (0.5% $_{w/v}$ Difco Yeast extract, 2% glucose) in 500 ml Erlenmeyer flasks with four aeration baffles) and incubated for 72 hours at 180 rpm on a rotary shaker at 30° C. The suspension was then centrifuged for 5 min at 5000 rpm at 4° C. on a Sorvall centrifuge and the medium was discarded. The cell pellet was resuspended in 200 ml minimal medium (0.67% $_{w/v}$ Difco Yeast Nitrogen Base w/o Amino acids, 1.00% ($Na_2$-Succinate), 0.2% saccharose) and culturing was continued for 6 hours in 500 ml Erlenmeyer flasks with four aeration baffles at 30° C. Thereafter, another 0.4% $_{w/v}$ saccharose (4 ml of sterile 20% saccharose solution) was added and shaking was continued over night on a rotary shaker at 30° C. at 180 rpm. The cells were washed three times with ice cold distilled water and centrifuged each time 5 min at 5000 rpm.

As model doughs, an ordinary pizza-recipe was chosen with a relatively strong flour. The ingredients were as follows:

| Ingredient | amount |
|---|---|
| Flour/type "Parisiennne" | 120.4 g |
| Tap water | 58.4 g |
| NaCl | 2.8 g |
| Peanut oil | 14.4 g |
| Yeast slurry in tap water 15% dry matter | 4.0 ml |
| Total | 200 g |

The dough was prepared as follows. All ingredients were kept at 4° C. and the dough preparation was performed in a refrigerated (4° C.) room. The peanut oil was liquefied by putting it for 30 min at room temperature. The yeast slurry was prepared by weighing few gram of yeast cake (approx. 30% dry matter) into a 50 ml Falcon polypropylene tube. An equal volume of cold tap water was added to obtain a slurry of approximately 15% dry matter and the slurry was vigorously mixed. The flour and salt was mixed and the peanut oil and water was added whereupon 4 ml of the yeast slurry as prepared above was added. The dough was kneaded for 4 min with a flat beater attachment to obtain a smooth dough. 100 g pieces were cut off, which were transferred to a glass measuring jar of the RISOGRAPH. The measurements were started immediately after sealing the measuring jar.

The gas development was measured at 8° C. at intervals of 1 hr over a time period of 120 hrs. The temperature was raised to 12° C. and gas development was measured at intervals of 1 hr over a time period of 100 to 120 hrs. The temperature was raised to 30° C. and gas development was measured at intervals of 10 min over a time period of 6 to 17 hrs. The gas development was calculated as the initial slopes of the gas curves at each temperature.

Figure 1:
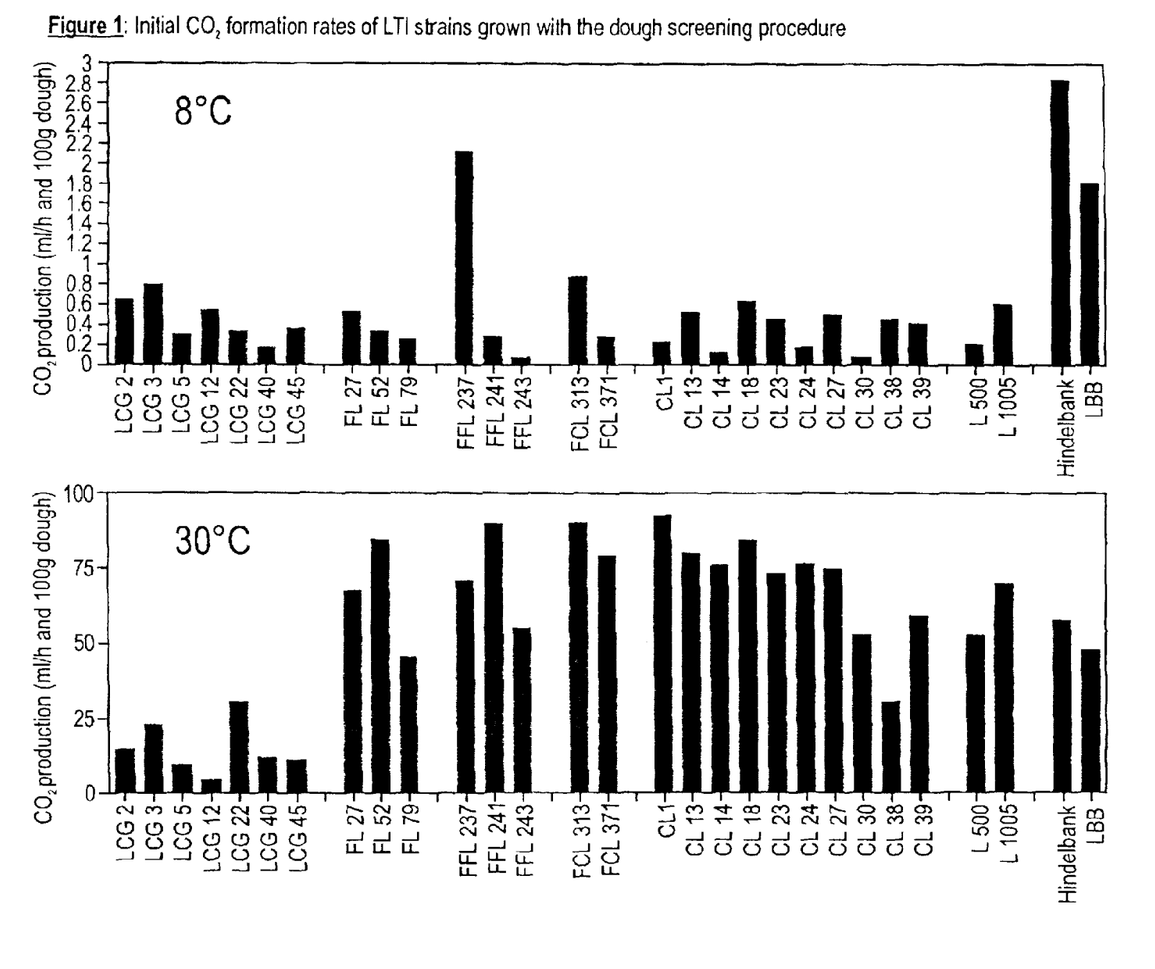
FIG. 1 shows the $CO_2$ production of yeast strains grown with the dough screening procedure obtained at 8° C. and 30° C., respectively, according to the invention.

The results of the measurements at 8° C. and 30° C. are shown in FIG. 1.

Example 4
A Dough Including Yeast According to the Invention

A model dough was prepared using the ingredients in the amounts as listed:

| Ingredient | parts by weight | % |
|---|---|---|
| Flour (Brüggmühle, type 400, Goldach, CH) | 100 | 64.48 |
| Salt (NaCl) | 2.48 | 1.60 |
| Ethanol | 1.63 | 1.05 |
| Water | 50.74 | 32.74 |
| Yeast dry matter (lti-strain FCL3 13) | 0.23 | 0.15 |

The dough was divided into aliquots of 100 g and introduced into the vessels of the "Niesler" (available from Biospectra AG, Schlieren (CH), wherein the dough composition was held over a time period of 4 weeks at a temperature of about 8° C. During said time period the development of $CO_2$ was measured. The results of these measurements are shown in FIG. 1. When baking the dough prepared in this manner after 1, 2, 3, 4 or 5 weeks the product showed an excellent texture and flavor that was comparable to that of products prepared from freshly mixed dough compositions.

Figure 2:
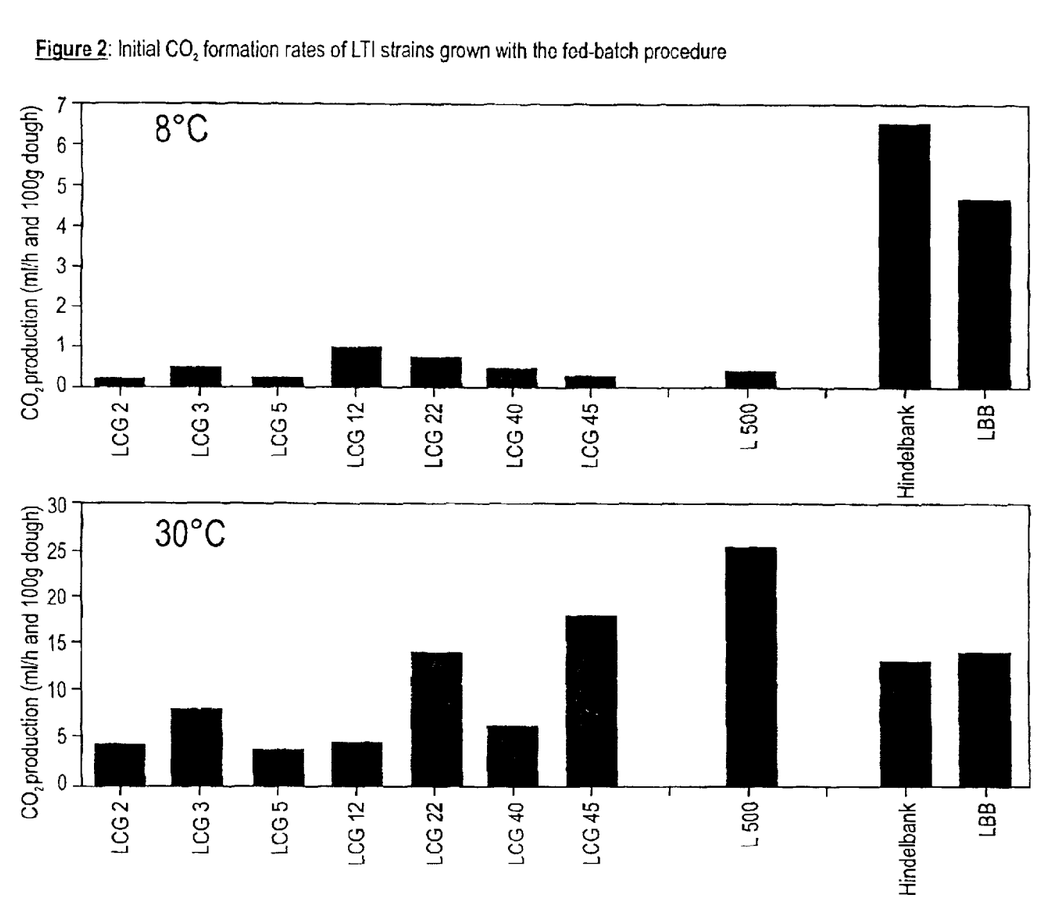
FIG. 2 shows a graph illustrating the production of $CO_2$ of different yeast strains grown with the fed-batch procedure obtained at 8° C. and 30° C., respectively, according to the invention.
Figure 3:
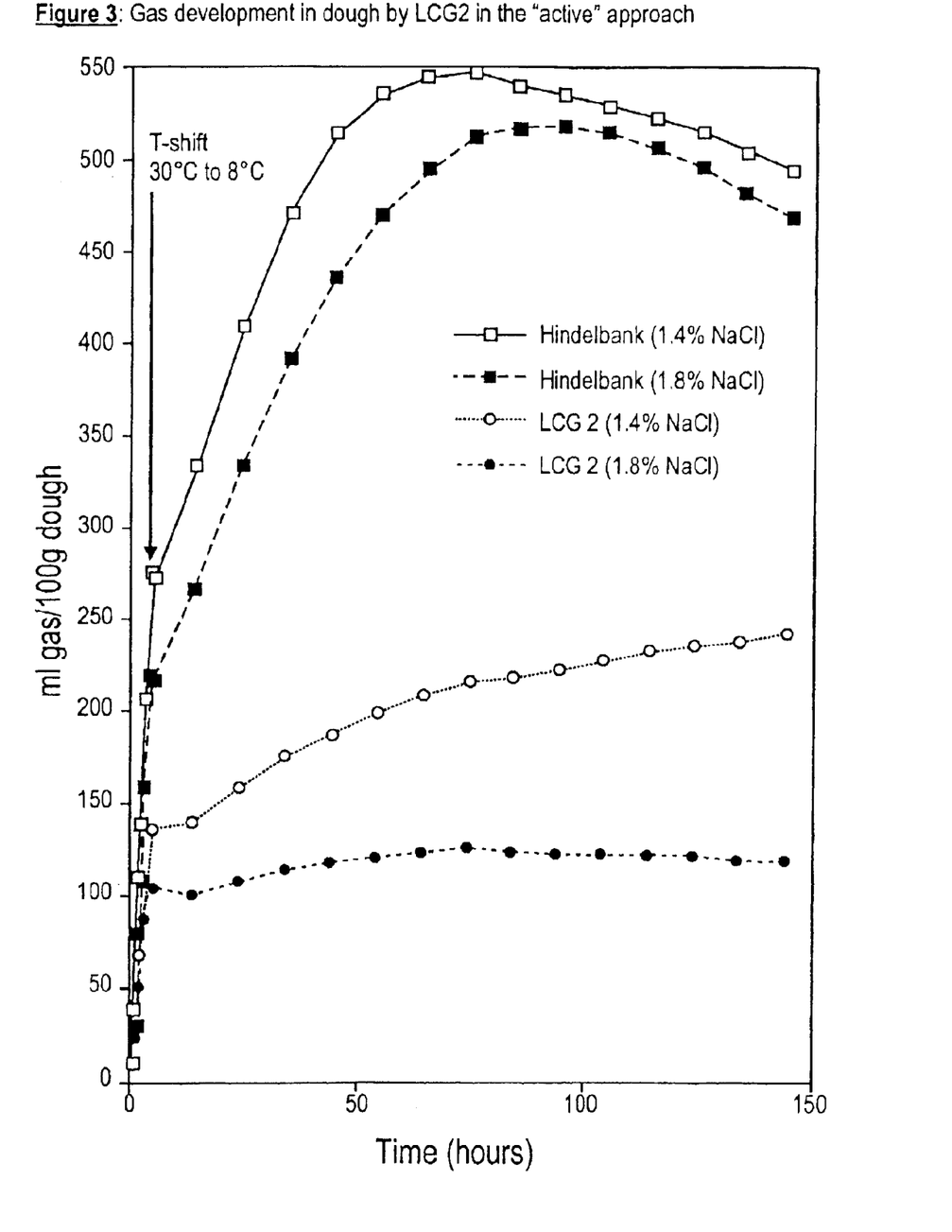
FIG. 3 shows a graph illustrating the production of $CO_2$ of different yeast strains at different temperatures in relative rates using the active approach according to the invention.

The results of measuring the $CO_2$ production for different yeast strains grown with the fed-batch procedure obtained at 8° C. and 30° C. are shown in FIG. 2. FIG. 3 illustrates the $CO_2$ production of different yeast strains at different temperatures in relative rates using the active approach according to the invention.

While it is apparent that the illustrative embodiments of the invention disclosed herein fulfill the objectives stated above, it is appreciated that numerous modifications and other embodiments may be devised by those of ordinary skill in the art. Therefore, it will be understood that the appended claims are intended to cover all such modifications and embodiments which would come within the spirit and scope of the present invention.

What is claimed is:

1. A stable, modified industrial baker's yeast having a low temperature inactive (lti)-property, wherein the modified baker's yeast is FCL 313 (NCIMB 41002), CL14 (NCIMB 41032), or CL18 (NCIMB 41033).

2. A stable, modified industrial baker's yeast comprising a low temperature inactive (lti)-property characterized by having a $CO_2$ production of less than about 1 ml/g dough per hour at refrigeration temperatures from about 3° C. to 12° C., wherein the baker's yeast is derived from a sporulated tetraploid zygote yeast and is accession number FCL 313 (NCIMB 41002), CL14 (NCIMB 41032). or CL18 (NCIMB 41033).

3. The baker's yeast of claim 2, wherein the baker's yeast is diploid or tetraploid.

4. The baker's yeast of claim 2, wherein the baker's yeast constitutively or inducibly expresses maltase.

5. A baker's yeast comprising a low temperature inactive (lti)-property characterized by having a $CO_2$ production of less than about 1 ml/g dough per hour at refrigeration temperatures from about 3° C. to 12° C. obtained by a method which comprises the following steps:
  selecting a yeast having a lti-property based on a recessive allele;
  diploidizing the selected yeast and selecting a homozygous mating type from the diploidized yeast;
  diploidizing an industrial baker's yeast and selecting a homozygous mating type from the diploidized industrial baker's yeast;

mating the diploidized yeast and the diploidized industrial baker's yeast having an opposite mating type to obtain a tetraploid zygote;

sporulating the tetraploid zygote; and selecting the sporulated zygote strains exhibiting the lti property to provide the modified stable industrial baker's yeast having the lti-property, wherein the baker's yeast obtained is accession number FCL 313 (NCIMB 41002). CL14 (NCIMB 41032), or CL18 (NCIMB 41033).

6. The baker's yeast of claim 5, wherein the recessive allele includes at least one gene which comprises a catabolite repressor gene, a gene coding for neutral or acid trehalase, a gene coding for a biosynthetic enzyme, or a gene that in allelic form(s) leads to an lti-property.

7. The baker's yeast of claim 5, wherein the baker's yeast constitutively or inducibly expresses maltase.

8. The baker's yeast of claim 5, wherein the baker's yeast is diploid or tetraploid.

* * * * *